(12) United States Patent
Glace et al.

(10) Patent No.: US 10,143,583 B2
(45) Date of Patent: Dec. 4, 2018

(54) LUMBAR BRACE

(71) Applicant: Corflex, Inc., Manchester, NH (US)

(72) Inventors: Benjamin Glace, Dunbarton, NH (US); Steven Santaniello, Cranston, RI (US); Rita Carney, Auburn, NH (US)

(73) Assignee: Corflex, Inc., Manchester, NH (US)

( * ) Notice: Subject to any disclaimer, the term of this patent is extended or adjusted under 35 U.S.C. 154(b) by 434 days.

(21) Appl. No.: 14/995,614

(22) Filed: Jan. 14, 2016

(65) Prior Publication Data

US 2016/0206467 A1 Jul. 21, 2016

Related U.S. Application Data

(60) Provisional application No. 62/104,269, filed on Jan. 16, 2015.

(51) Int. Cl.
*A61F 5/02* (2006.01)

(52) U.S. Cl.
CPC ............... *A61F 5/028* (2013.01); *A61F 5/02* (2013.01)

(58) Field of Classification Search
CPC .................................. A61F 5/02; A61F 5/028
USPC .......................................................... 602/19
See application file for complete search history.

(56) References Cited

U.S. PATENT DOCUMENTS

| | | | | |
|---|---|---|---|---|
| 3,434,469 A | * | 3/1969 | Swift | A61F 5/028 602/19 |
| 5,207,635 A | * | 5/1993 | Richards | A61F 5/028 128/876 |
| 5,437,614 A | * | 8/1995 | Grim | A61F 5/022 602/19 |
| 5,722,940 A | * | 3/1998 | Gaylord, Jr. | A61F 5/028 128/96.1 |
| 6,213,968 B1 | | 4/2001 | Heinz et al. | |
| 8,372,023 B2 | * | 2/2013 | Garth | A61F 5/028 128/876 |
| 2005/0059917 A1 | | 3/2005 | Garth et al. | |
| 2011/0213284 A1 | | 9/2011 | Garth et al. | |
| 2014/0135672 A1 | | 5/2014 | Joseph et al. | |

* cited by examiner

*Primary Examiner* — Keri J Nelson
(74) *Attorney, Agent, or Firm* — Davis & Bujold, P.L.L.C.; Kimberly A. Peaslee (57) ABSTRACT

An adjustable lumbar support system with independent lacer guides and a hinged portion. An adjustable lumbar support system having phase change material and/or removable stays. An adjustable lumbar support system having one or more panels, with or without perforations, to provide for improved adjustability for patient comfort and compliance. An adjustable lumbar support system having a pleated or quilted central portion.

10 Claims, 7 Drawing Sheets

LUMBAR BRACE

CROSS REFERENCE TO RELATED APPLICATIONS

This application claims the benefit of U.S. Provisional Application No. 62/104,269, filed Jan. 16, 2015, the contents of which are incorporated by reference herein in their entirety.

FIELD OF THE INVENTION

The present disclosure relates to orthotic braces and more particularly to lumbar, thoracic, and sacral orthoses.

BACKGROUND OF THE INVENTION

There are many forms of orthoses, or devices used externally to modify the structure and/or function of the skeletal and/or neuromuscular systems of the body. For example, there are orthoses that are applied to the neck, to the spine, to the upper limbs, and to the lower limbs. Additionally, there are many different purposes for using orthoses ranging from rehabilitative to prophylactic. Rehabilitative braces are typically used to limit the movement of a portion of the body following an injury or a surgery.

Orthoses can be used for many purposes. Orthoses can restrict movement in one or more directions, immobilize an area of the body, assist movement of a particular joint or region of the body, reduce the forces applied to an area of the body, aid rehabilitation by preventing reinjury, correct the motion of a portion of the body to reduce pain or improve function, and the like.

SUMMARY OF THE INVENTION

One aspect of the present disclosure is an adjustable lumber brace comprising, a center portion having a central portion, a first end, a second end, a top edge and a bottom edge; two belt loops, where one is affixed to the first end and the other is affixed to the second end of the center portion; four lacer guides affixed individually between the first and second ends and the central portion, wherein the lacer guides are located along the top and bottom edges and the lacer guides and further comprise a central anchor point for the attachment of laces; two side portions that are removably attached to the belt loops; and one or more panels which are associated with the center portion.

One embodiment of the adjustable lumbar brace is wherein the center portion comprises phase change material.

One embodiment of the adjustable lumbar brace is wherein the center portion comprises stays.

One embodiment of the adjustable lumbar brace is wherein the central portion is quilted or pleated.

One embodiment of the adjustable lumbar brace is wherein the one or more panels has one or more perforations.

One embodiment of the adjustable lumbar brace is wherein the one or more panels has one or more cutout regions.

Another aspect of the present disclosure is an adjustable lumber brace comprising, a center portion having a central portion, a first end, a second end, a top edge and a bottom edge; two side portions, where one is affixed to the first end and the other is affixed to the second end of the center portion; four lacer guides affixed individually between the first and second ends and the central portion, wherein the lacer guides are located along the top and bottom edges and the lacer guides and further comprise a central anchor point for the attachment of laces; and one or more panels which are associated with the center portion.

One embodiment of the adjustable lumbar brace is wherein the center portion comprises phase change material.

One embodiment of the adjustable lumbar brace is wherein the center portion comprises stays.

One embodiment of the adjustable lumbar brace is wherein the central portion is quilted or pleated.

One embodiment of the adjustable lumbar brace is wherein the one or more panels has one or more perforations.

One embodiment of the adjustable lumbar brace is wherein the one or more panels has one or more cutout regions.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE INVENTION

Certain lumbar and sacral orthoses are used to partially or fully immobilize the trunk (or torso) for a number of purposes including protection after surgery or injury as well as prophylactically to prevent injury or reinjury during activities that typically cause back injuries. Orthoses are also used to protect a wide variety of structures, not just the vertebrae, including intervertebral discs, nerves, the spinal cord, ligaments, muscles, and the like. When worn during the acute stage, post-surgical or post-injury, a brace is typically worn whenever the patient is upright and/or ambulatory (e.g., when out of bed) to protect and stabilize the surgical/injury site. When worn prophylactically, a brace is typically only worn during specific activities to prevent deterioration of the trunk musculature. Braces can vary in height, which can determine the amount of immobilization provided. In certain embodiments, this variation in height will control sagittal plane motion or flexion and extension of the spine. In certain embodiments, a shorter brace limits motion in the lumbar and upper sacral region, while a taller brace limits motion in the lower thoracic, lumbar, and upper sacral vertebrae. In certain embodiments, extensions can be added to orthoses of the present disclosure to control coronal plane motion or side-bending.

Another use of orthoses, as described herein, is in spinal unloading. This application is based on the premise that increasing intra-abdominal pressure results in decreased compressive forces. This is achieved using anterior and posterior panels along with a rigid belt to deliver a compressive force to the abdominal cavity. When the belt is tightened, compressive forces are applied to the trunk of the patient.

There are numerous indications for spinal bracing as described herein, including, but not limited to, acute and chronic strains or sprains in the torso area, postural correction, spinal unloading, degenerative disc disease, post-surgical fusion, laminectomy or discectomy, congenital or traumatic instability, herniated disc(s), spinal stenosis, fractures, spondylolisthesis, spondylolysis, spondylosis, and facet syndrome.

It is understood, that in an effort to maximize the benefits of an orthopedic brace it must be properly fitted and adjusted to the patient. Adjustment variables include fitting patients of various sizes and body proportions, and accommodating a variety of possible surgical or injury sites. The adjustment of the brace will also be continual as the patient heals and can tolerate larger ranges of motion, as swelling is reduced, and the like. At times, there may also be readjustment of the braces to adapt to add-on accessories or product upgrades.

To adjust around the lumbar and sacral regions of a patient, some brace designs utilize lacer guides that are located along the edge of an opening, or gap, in the brace. For example, in U.S. Pat. No. 6,213,968 the lacer guides are located alongside a gap in the brace, which may also contain wing portions made of "moderately rigid plastic material." Additionally, the lacer guides in U.S. Pat. No. 6,213,968 are detachable. This modularity can create errors in alignment and a lack of reproducibility of fit for the patient which can lead to prolonged healing times and/or patient non-compliance.

Similarly, U.S. Patent Pub. No. 2014/0135672 comprises lacer guides adjacent to an opening of the brace and provides add-on "posterior pads" that can include rigid supports, but that are designed to more independently of the brace as the brace is tightened. In U.S. Patent Pub. No. 2014/0135672, the brace requires fitting by a medical professional or with complicated user instructions. In contrast, the brace of the present disclosure comprises a single unit that provides for a more accurate fit while providing for an ease of use not seen in prior art systems.

Another existing adjustment method utilizes lacer guides that are rigidly attached to each other and to a lateral support as disclosed in U.S. Patent Pub. No. 2011/0213284. There, the tightening of the laces creates a curvature in the rigid material that the lacer guides are attached to. This curvature is fixed based on the properties of the rigid material used to create the supports to which the lacer guides are affixed. Thus, this curvature provides for some adjustability but only within a narrow range. In contrast, the brace of the present disclosure provides for a more accurate fit by providing lacer guides that can move independently of each other. Additionally, the brace of the present disclosure provides for a hinged portion located proximal to the lacer guides, but not connected to the guides, to provide for additional range of motion and conformability of the brace to each individual patient, regardless of body shape and size.

Figure 1A:
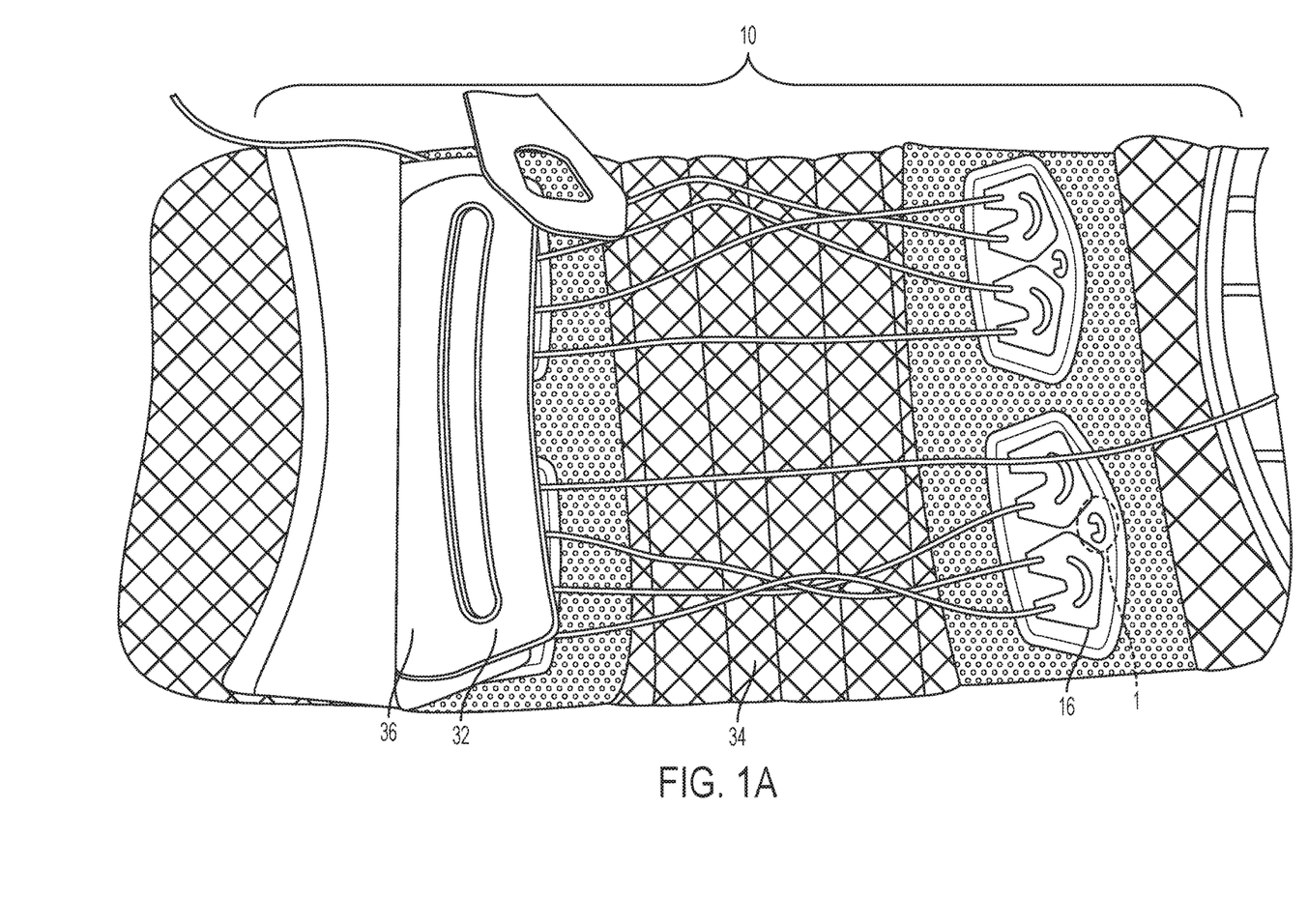
FIG. 1A shows a portion of one embodiment of an adjustable orthotic brace of the present disclosure from the side facing away from the patient.
Figure 1B:
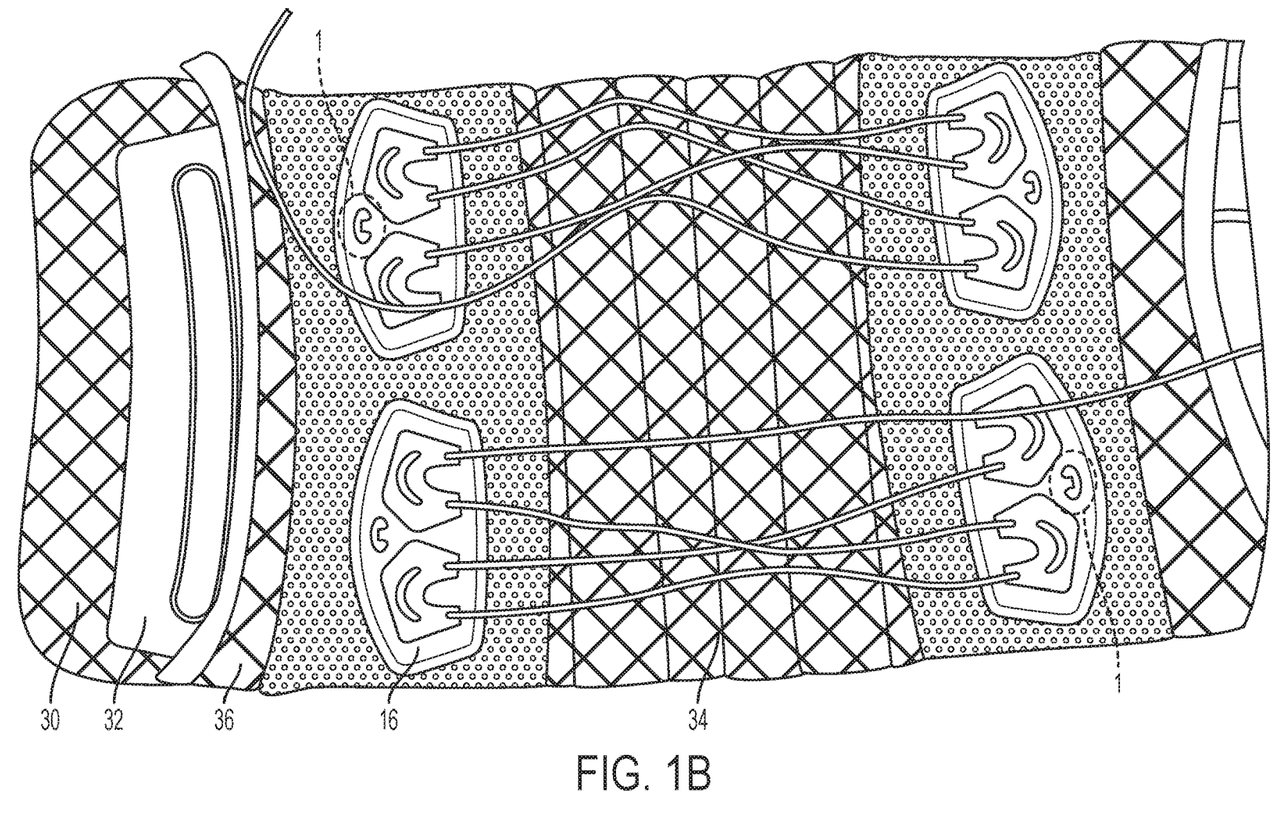
FIG. 1B shows a portion of one embodiment of an adjustable orthotic brace of the present disclosure from the side facing away from the patient.

One aspect of the present disclosure is an adjustable lumbar sacral orthopedic brace where the lacer guides act as independent anchors. Referring to FIGS. 1A and 1B, portions of one embodiment of an adjustable orthotic brace of the present disclosure are shown from the side facing away from the patient. More specifically, in certain embodiments of the orthotic brace of the present disclosure lacer guides 16 contain a central anchor point 1 where the laces attach to the lacer guide. In certain embodiments, the lacing is anchored in the center of the lacer guide 16 and not on an outside or inside edge. In certain embodiments, the central anchor point creates additional degrees of freedom, such that the lacer guides can rotate as needed about the central anchor point, which can act as a pivot. In certain embodiments, the single mount also provides for greater ease of movement.

In certain embodiments, individual lacer guides are provided as part of a modular design. The modularity allows for better conformance to the patient's body. In certain embodiments, the lacer guides are configured to move not only along the horizontal axis during tightening as the main function of the brace, but also to move in the vertical direction to fit a patient's anatomy, as needed. In certain embodiments, better conformity around the pulleys further compensates for any asymmetrical and/or added bandaging or hot/cold therapy packs that may be needed by the patient to provide for better fit and greater comfort.

In certain embodiments, the lacer guides rotate slightly as well. Depending on the type of textile used, one can design in a desired amount of rotation. Textile variation can include open weaves, meshes, Lycra, elastic materials, and the like. Textile weave directions can also be specified to help facilitate this attribute. It is also within the scope of this disclosure that the fabric used in the manufacture of the brace is computer (CAD) woven to create desired amounts of control in any direction depending on the desired characteristics.

In certain embodiments of the present disclosure, the orthotic brace has a central portion 10 upon which the lacer guides 16 are affixed in an orientation around a quilted, or pleated, portion 34. In certain embodiments, belt loops 32 are affixed 36 to provide a hinge motion independent of the lacer guides 16. In certain embodiments, there is additional fabric or material adjacent to the belt loops to provide a comfortable boundary between the patient and the attachment portion 36 of the belt loop 32. See, for example, FIG. 3, #12. In certain embodiments, the hinged portions allow for better conformance around a patient's waistline because the belt loops are not rigidly mounted. In certain embodiments, the hinged portion is mounted to flexible portions of the brace separate from the lacer guides and stays.

Still referring to FIGS. 1A and 1B, certain embodiments of the present disclosure are configured so that all four lacer guides bend or move independent of each other. The lacer guides 16 can move left to right and top to bottom when each lace is tightened. Additionally, due to the construction of the lacer guides 16 and their independence with respect to each other, the brace provides for greater range of motion for each independent lacer guide, which provides for greater adjustability, and thus fit a greater range of patients. In certain embodiments, each lacer guide is stitched around its perimeter and onto the back portion of the brace. See, FIGS. 1A and 1B.

In certain embodiments, the brace is tightened using a slide through angled strap 18. The strap is angled and positioned so that the hand can enter into the component at an ergonomic and natural entry angle. This is particularly important for wounded, elderly or arthritic patients. In certain embodiments, the strap is open on both sides and is stitched in the middle to keep it close to the brace, thus reducing catch points and keeping the user's hand tighter, which provides for better ease of use, particularly for users needing to use a variety of hand postures. This configuration provides more variation to people with injuries or arthritis of the hand and thumb.

Figure 2:
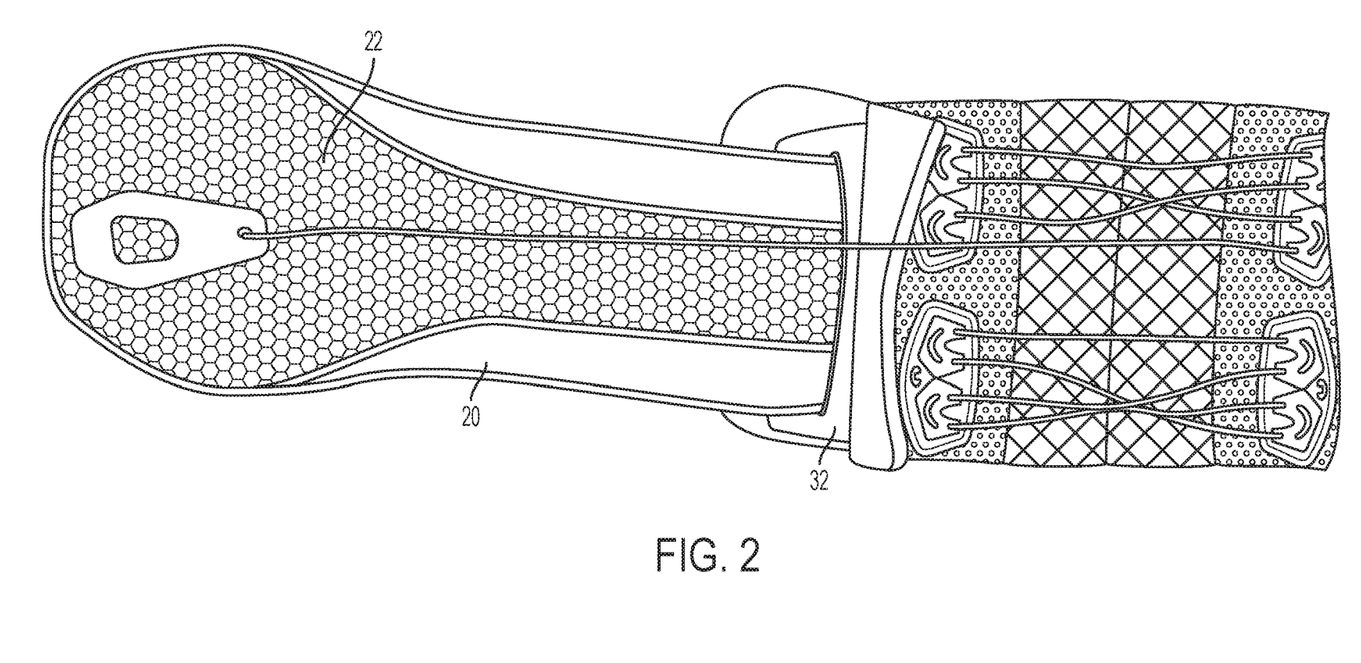
FIG. 2 shows a portion of one embodiment of an adjustable orthotic brace of the present disclosure from the side facing away from the patient.

Referring to FIG. 2, a portion of one embodiment of an adjustable orthotic brace of the present disclosure is shown from the side facing away from the patient. More specifically, in certain embodiments the brace of the present disclosure comprises two side portions 20, which are attachable to the belt loops 32 via hook and loop 22 (or other mechanisms known to those of skill in the art) and which can be interchanged to provide braces of varying overall lengths, if needed. These braces will then better fit patients of varying sizes and shapes. In certain embodiments, the side portions attach using a belt loop 32 which is separate from the lacer guides 16 and as such, the lacer guides 16 can move vertically in reference to each other as well as independently from the belt loop 32. The separation of the belt loop and the lacer guides also provides a hinged portion for better fit and comfort for the patient. See also, FIGS. 1A and 1B.

Figure 3:
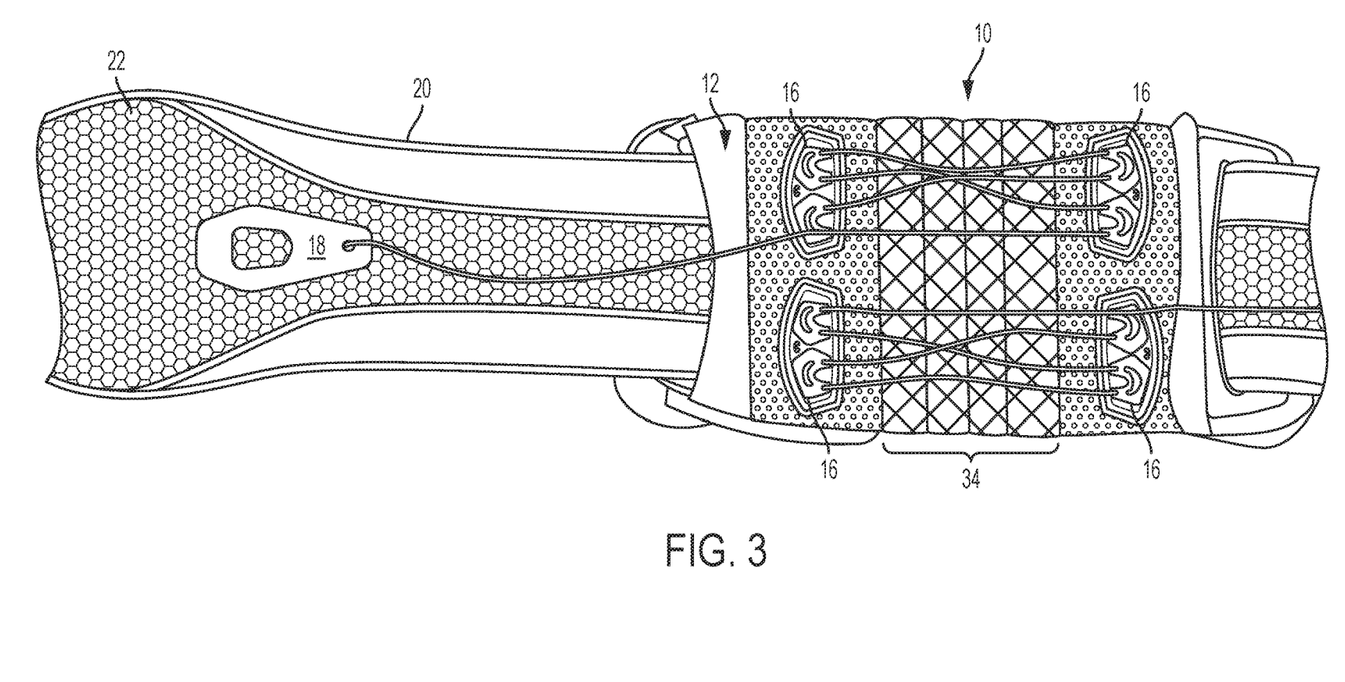
FIG. 3 shows a portion of one embodiment of an adjustable orthotic brace of the present disclosure from the side facing away from the patient.

Referring to FIG. 3, a portion of one embodiment of an adjustable orthotic brace of the present disclosure is shown from the side facing away from the patient. More specifically, in certain embodiments the central section 34 of the back panel 10 of the brace is quilted, or pleated, to provide additional flexibility and additional compressibility to mitigate bunching, which can be painful to the patient and can reduce compliance. Additionally, bulging or bunching can provide undesirable and/or improper pressure when a user moves, or sits down, while wearing the brace. In addition to being painful, bunching along the sides of the back panel, as seen in prior art systems such as U.S. Patent Pub. No. 2005/0059917, can reduce the ability to fine-tune the fit of the brace by providing for greater tightening on one side of the brace as compared to the other side when the two pulleys are tightened, thus creating misalignments.

Figure 4:
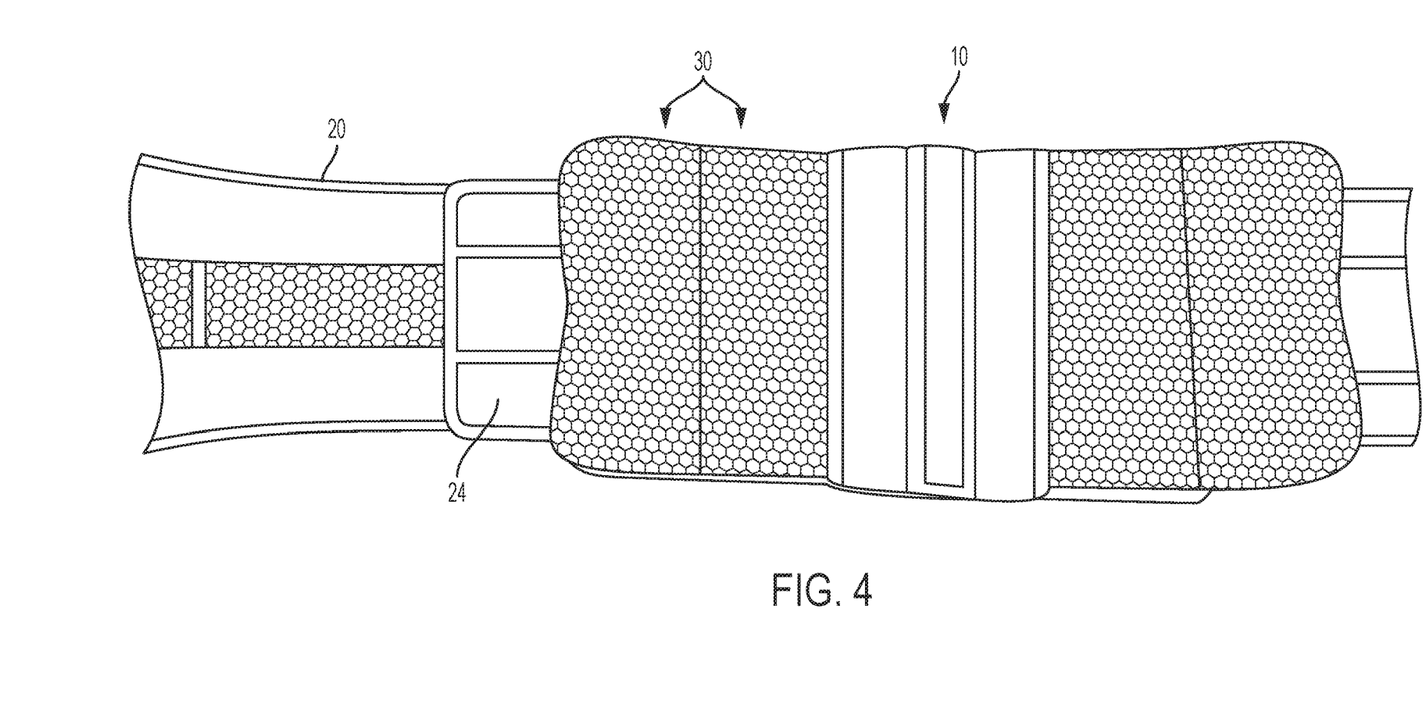
FIG. 4 shows a portion of one embodiment of an adjustable orthotic brace of the present disclosure from the side facing toward the patient.
Figure 5A:
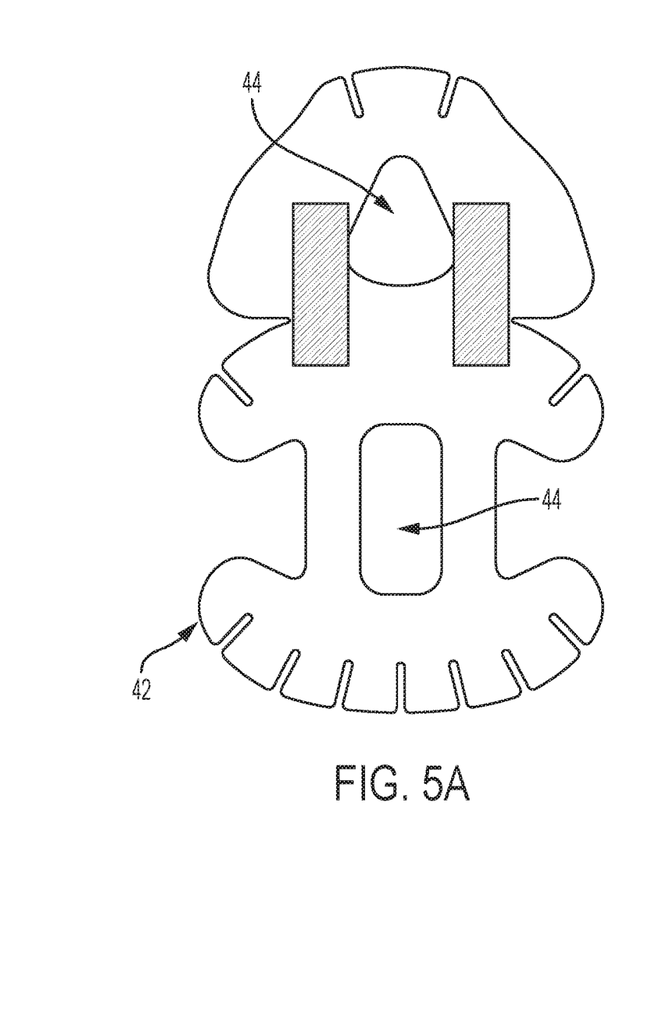
FIG. 5A shows a front view of an embodiment of a panel for an adjustable orthotic brace of the present disclosure.
Figure 5B:
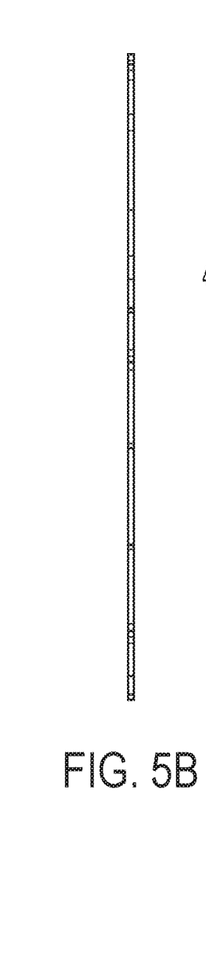
FIG. 5B shows a side view of an embodiment of a panel for an adjustable orthotic brace of the present disclosure.
Figure 5C:
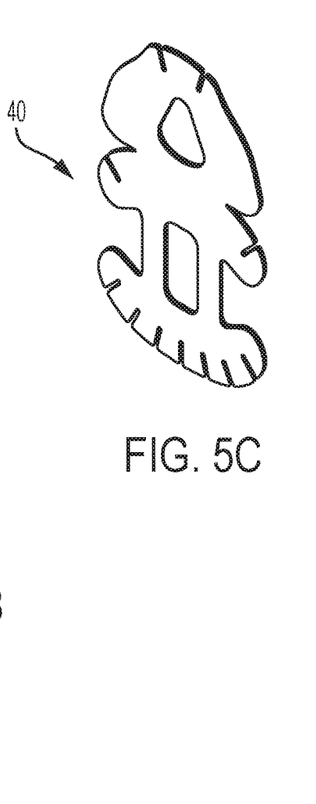
FIG. 5C shows a perspective view of an embodiment of a panel for an adjustable orthotic brace of the present disclosure.
Figure 6A:
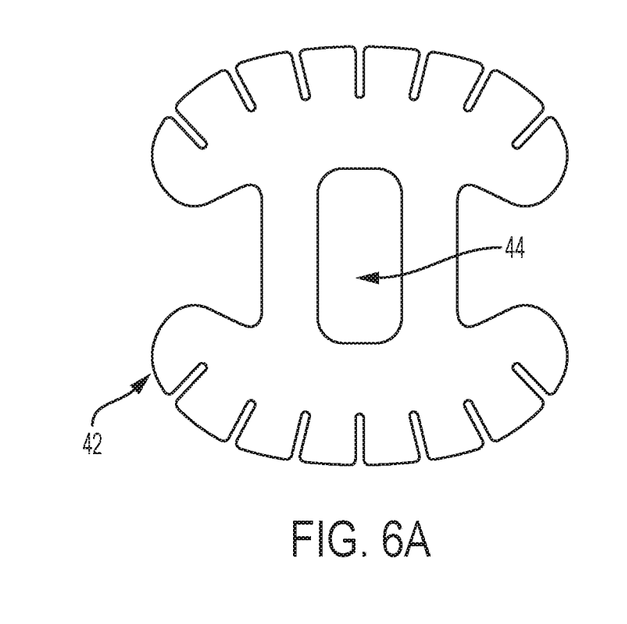
FIG. 6A shows a front view of an embodiment of a panel for an adjustable orthotic brace of the present disclosure.
Figure 6B:
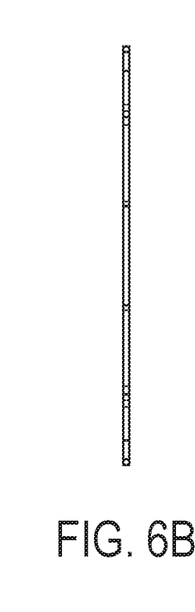
FIG. 6B shows a side view of an embodiment of a panel for an adjustable orthotic brace of the present disclosure.
Figure 6C:
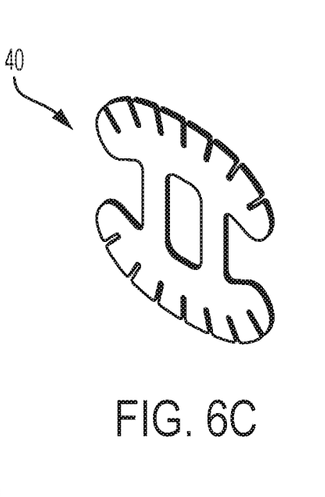
FIG. 6C shows a perspective view of an embodiment of a panel for an adjustable orthotic brace of the present disclosure.

Referring to FIG. 4, a portion of one embodiment of an adjustable orthotic brace of the present disclosure is shown from the side facing the patient's body. More specifically, in certain embodiments of the present disclosure a gel pack can be inserted into or attached to the center back portion (gel pack not shown). In certain embodiments, portions 30 of the center portion 10 of the brace can be constructed of heat sink materials, phase change materials, and the like. In certain embodiments, the side portions 20 are adjustable 24 using a hook and loop material, or the like.

In certain embodiments of the brace of the present disclosure, modular stays can be inserted in the back portion (stays not shown). In certain embodiments, stays are installed in a closeable pocket, or the like. In certain embodiments, the stays are removable and/or customizable by heat forming. In certain embodiments of the brace of the present disclosure, removable stays allow the separate molded belt loops to act as a secondary support system. As the patient heals and needs less support this creates another level of customization for the user. The brace of the present disclosure differs from other systems that incorporate stays and pulleys into a single molded component. The level of component customization of the present disclosure is significant since the brace may be worn by the patient many years after surgery or injury.

Referring to FIGS. 5A-5C and 6A-6C, embodiments of panels 40 for the adjustable orthotic braces of the present disclosure are shown. In certain embodiments, additional panels can be attached to and/or inserted into the center portion 10 of the brace. This modularity provides adjustability, ease of manufacture, ease of use, and the like. In certain embodiments, the panels are constructed to be perforated 42 so that when a patient sits down or moves around, the panel does not cut into the patient's body. As used herein, perforation means a hole or region made by boring or piercing, or the like, to create an aperture passing through or into something. In certain embodiments of the present disclosure perforations can comprise a small hole or row of small holes. In certain embodiments, the perforations 42 can act like fingers that can move independently of each other and provide improved adjustability and comfort for the wearer. Increasing the comfort of the brace and the panels, increases patient compliance. Increasing patient compliance can help speed recovery.

In certain embodiments, the panels 40 are interchangeable to allow for ease of assembly and adaptability for different applications. In certain embodiments, there is a split fabric panel, or pocket, allowing for ease of panel removal. In certain embodiments, the pocket is removable. In certain embodiments, the panels have varied geometry, such that the panel is still flexible where needed, but the stacked portion adds rigidity for much needed support in the upper portion of the back panel that is less controlled by the lacer guide system, thus reducing movement in the direction associated with a patient leaning back. In certain embodiments, finger-like protrusions 42 help add a combination of flexibility and rigidity to minimize patient discomfort. In certain embodiments, center cutouts 44 on the panel can reduce pressure along the middle of the spine, which typically is co-localized with the surgical site, which can also improve comfort and patient compliance.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:
1. An adjustable lumber brace comprising,
a fabric center portion of the lumbar brace having a central quilted or pleated portion, a first end, a second end, a top edge and a bottom edge;

a first and a second belt loop, where the first belt loop is affixed to the first end of the fabric center portion and the second belt loop is affixed to the second end of the fabric center portion;

a first lacer guide comprising two lobes and a central anchor point for the attachment of a lace, wherein the first lacer guide is affixed to the first end along the top edge of the fabric center portion of the lumbar brace;

a second lacer guide comprising two lobes and a central anchor point for the attachment of a lace, wherein the second lacer guide is affixed to the first end along the bottom edge of the fabric center portion of the lumbar brace;

a third lacer guide comprising two lobes and a central anchor point for the attachment of a lace, wherein the third lacer guide is affixed to the second end along the top edge of the fabric center portion of the lumbar brace;

a fourth lacer guide comprising two lobes and a central anchor point for the attachment of a lace, wherein the fourth lacer guide is affixed to the second end along the bottom edge of the fabric center portion of the lumbar brace;

a first and a second side portion, wherein the first side portion is removably attached to the first belt loop and the second side portion is removably attached to the second belt loop, thereby forming an adjustable length lumbar brace; and one or more panels which are removably associated with the center fabric portion.

2. The adjustable lumbar brace of claim 1, wherein the center fabric portion comprises phase change material.

3. The adjustable lumbar brace of claim 1, wherein the center fabric portion comprises stays.

4. The adjustable lumbar brace of claim 1, wherein the one or more panels has one or more perforations.

5. The adjustable lumbar brace of claim 1, wherein the one or more panels has one or more cutout regions.

6. An adjustable lumber brace comprising, a fabric center portion of the lumbar brace having a central quilted or pleated portion, a first end, a second end, a top edge and a bottom edge;

a first and a second side portion, wherein the first side portion is affixed to the first end of the center portion and the second side portion is affixed to the second end of the center portion, thereby forming an adjustable length lumbar brace;

a first lacer guide comprising two lobes and a central anchor point for the attachment of a lace, wherein the first lacer guide is affixed to the first end along the top edge of the fabric center portion of the lumbar brace;

a second lacer guide comprising two lobes and a central anchor point for the attachment of a lace, wherein the second lacer guide is affixed to the first end along the bottom edge of the fabric center portion of the lumbar brace;

a third lacer guide comprising two lobes and a central anchor point for the attachment of a lace, wherein the third lacer guide is affixed to the second end along the top edge of the fabric center portion of the lumbar brace;

a fourth lacer guide comprising two lobes and a central anchor point for the attachment of a lace, wherein the fourth lacer guide is affixed to the second end along the bottom edge of the fabric center portion of the lumbar brace; and one or more panels which are removably associated with the center fabric portion.

7. The adjustable lumbar brace of claim 6, wherein the center fabric portion comprises phase change material.

8. The adjustable lumbar brace of claim 6, wherein the center fabric portion comprises stays.

9. The adjustable lumbar brace of claim 6, wherein the one or more panels has one or more perforations.

10. The adjustable lumbar brace of claim 6, wherein the one or more panels has one or more cutout regions.

* * * * *